(12) United States Patent
Xu et al.

(10) Patent No.: US 7,794,145 B2
(45) Date of Patent: Sep. 14, 2010

(54) MEDICAL TABLE AND X-RAY IMAGING APPARATUS

(75) Inventors: Jiake Xu, Beijing (CN); Bin Ye, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 8 days.

(21) Appl. No.: 12/238,176

(22) Filed: Sep. 25, 2008

(65) Prior Publication Data

US 2009/0086930 A1  Apr. 2, 2009

(30) Foreign Application Priority Data

Sep. 28, 2007  (CN) .......................... 200710161334

(51) Int. Cl.
*A61B 6/04* (2006.01)
(52) U.S. Cl. ................. 378/209; 5/601; 5/943
(58) Field of Classification Search ................ 378/209; 5/601, 943
See application file for complete search history.

(56) References Cited

U.S. PATENT DOCUMENTS

| | | | |
|---|---|---|---|
| 5,327,474 A | 7/1994 | Inoue et al. | |
| 5,475,884 A | 12/1995 | Kirmse et al. | |
| 5,661,772 A | 8/1997 | Bar et al. | |
| 5,822,814 A | 10/1998 | Van der Ende | |
| 5,832,056 A | 11/1998 | Mochitate et al. | |
| 6,027,247 A | 2/2000 | Tachi et al. | |
| 6,052,611 A | 4/2000 | Yanof et al. | |
| 7,264,396 B2 | 9/2007 | Jahrling | |
| 7,478,947 B2 * | 1/2009 | Kobayashi | 378/181 |

FOREIGN PATENT DOCUMENTS

JP  06-047040  2/1994

* cited by examiner

*Primary Examiner*—Jurie Yun
(74) *Attorney, Agent, or Firm*—Armstrong Teasdale LLP

(57) ABSTRACT

A medical table in which a top plate for a patient to lie on is supported by a pedestal base in a manner to be able to move parallel to a plate surface, includes a detecting device for detecting that fingers holding the top plate are about to collide against the pedestal base when moving the top plate, and a stopping device for stopping movement of the top plate according to a detection signal from the detecting device.

17 Claims, 7 Drawing Sheets

332

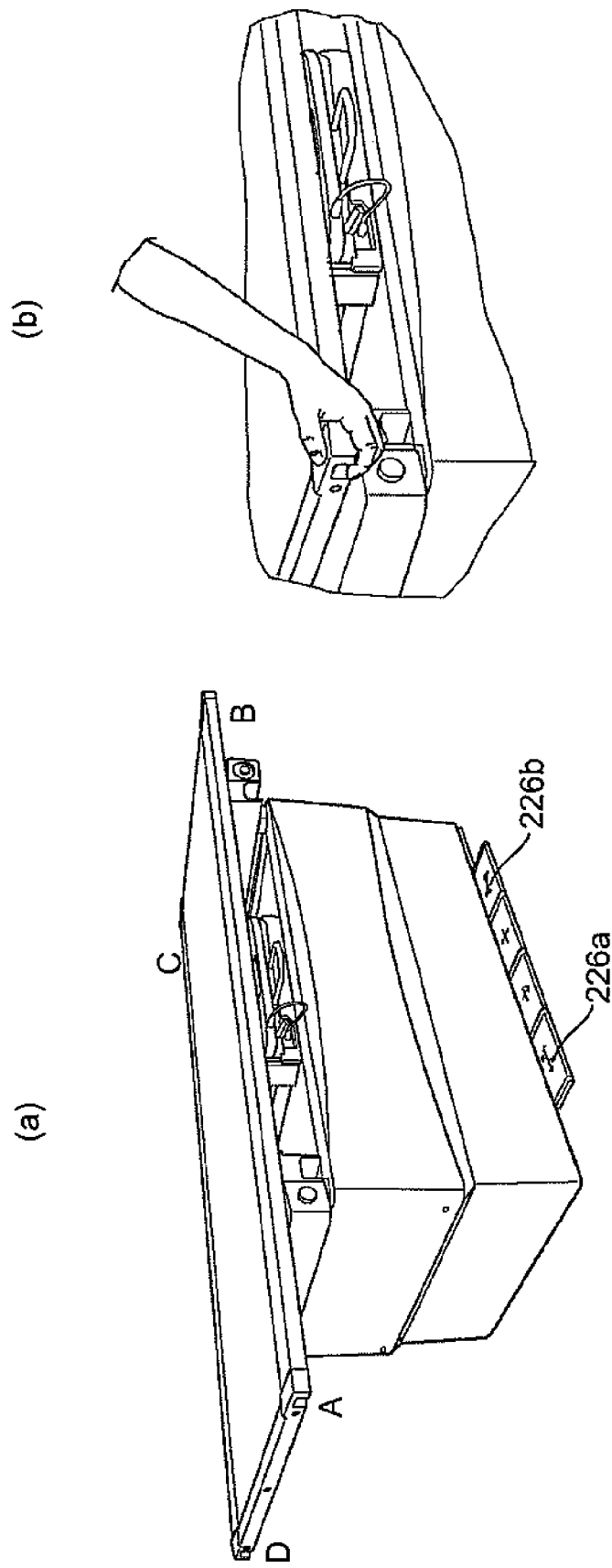

MEDICAL TABLE AND X-RAY IMAGING APPARATUS

CROSS REFERENCE TO RELATED APPLICATIONS

This application claims the benefit of Chinese Patent Application No. 200710161334.7 filed Sep. 28, 2007, which is hereby incorporated by reference in its entirety.

BACKGROUND OF THE INVENTION

The subject matter disclosed herein is related to a medical table and an X-ray imaging apparatus and more particularly to a medical table in which a top plate for a patient to lie on is supported by a pedestal base in a manner to be able to move parallel to a plate surface and an X-ray imaging apparatus having such a medical table.

A medical table used in X-ray photography is so constructed that a top plate for a patient to lie on is supported by a pedestal base. An X-ray receiver and an X-ray film cassette are provided in the pedestal base. The X-ray receiver and the like receive X rays coming through a patient and the top plate from an X-ray source. The top plate can move parallel to a plate surface over the pedestal base (For example, see Japanese Unexamined Patent Publication No. Hei 6(1994)-47040).

When moving the top plate manually, an operator holds an edge of the top plate or the like with fingers to move it. At this time, care must be taken not to hit the fingers against the pedestal base or jam the fingers. Particularly when moving the top plate with a patient on it, special care must be taken because it moves by inertia.

BRIEF DESCRIPTION OF THE INVENTION

It is desirable that the problem described previously is solved.

According to a first aspect, a medical table includes a top plate for a patient to lie on that is supported by a pedestal base in a manner to be able to move parallel to a plate surface, a detecting device for detecting that fingers holding the top plate are about to collide against the pedestal base when moving the top plate, and a stopping device for stopping movement of the top plate according to a detection signal from the detecting device.

According to a second aspect, in the medical table as described in the first aspect, the detecting device has a travel sensor that senses the fingers' travel toward a direction of collision against the pedestal base.

According to a third aspect, in the medical table as described in the second aspect, the travel sensor includes a linearly moving member which is given a recovery force by a spring, and a shift sensor which senses shift of the linearly moving member.

According to a fourth aspect, in the medical table as described in the third aspect, the linearly moving member has a contact plate for the fingers at one end.

According to a fifth aspect, in the medical table as described in the fourth aspect, the contact plate has a cushion member on a surface of it.

According to a sixth aspect, in the medical table as described in the fifth aspect, the cushion member is made of rubber.

According to a seventh aspect, in the medical table as described in the third aspect, the shift sensor senses shift of the other end of the linearly moving member.

According to an eighth aspect, in the medical table as described in the seventh aspect, the shift sensor is an optical sensor.

According to a ninth aspect in the medical table as described in the eighth aspect, the optical sensor includes a light-emitting element and a light-receiving element which face each other with a clearance between them, and a light-shielding element which enters or leaves the clearance.

According to a tenth aspect, in the medical table as described in the ninth aspect, the light-emitting element and the light-receiving element are fixed in position, and the light-shielding element moves together with the other end of the linearly moving member.

According to an eleventh aspect, an X-ray imaging apparatus includes a medical table in which a top plate for a patient to lie on is supported by a pedestal base in a manner to be able to move parallel to a plate surface, a photographing device for X-raying a patient lying on the medical table, a detecting device for detecting that fingers holding the top plate are about to collide against the pedestal base when moving the top plate, and a stopping device for stopping movement of the top plate according to a detection signal from the detecting device.

According to a twelfth aspect, in the X-ray imaging apparatus as described in the eleventh aspect, the detecting device has a travel sensor which senses the fingers' travel toward a direction of collision against the pedestal base.

According to a thirteenth aspect, in the X-ray imaging apparatus as described in the twelfth aspect, the travel sensor includes a linearly moving member which is given a recovery force by a spring, and a shift sensor which senses shift of the linearly moving member.

According to a fourteenth aspect, in the X-ray imaging apparatus as described in the thirteenth aspect, the linearly moving member has a contact plate for the fingers at one end.

According to a fifteenth aspect, in the X-ray imaging apparatus as described in the fourteenth aspect, the contact plate has a cushion member on a surface of it.

According to a sixteenth aspect, in the X-ray imaging apparatus as described in the fifteenth aspect, the cushion member is made of rubber.

According to a seventeenth aspect, in the X-ray imaging apparatus as described in the thirteenth aspect, the shift sensor senses shift of the other end of the linearly moving member.

According to an eighteenth aspect, in the X-ray imaging apparatus as described in the seventeenth aspect, the shift sensor is an optical sensor.

According to a nineteenth aspect, in the X-ray imaging apparatus as described in the eighteenth aspect, the optical sensor includes a light-emitting element and a light-receiving element which face each other with a clearance between them, and a light-shielding element which enters or leaves the clearance.

According to a twentieth aspect, in the X-ray imaging apparatus as described in the nineteenth aspect, the light-emitting element and the light-receiving element are fixed in position, and the light-shielding clement moves together with the other end of the linearly moving member.

According to the first aspect, a medical table in which a top plate for a patient to lie on is supported by a pedestal base in a manner to be able to move parallel to a plate surface, includes a detecting device for detecting that fingers holding the top plate are about to collide against the pedestal base when moving the top plate, and a stopping device for stopping movement of the top plate according to a detection signal from the detecting device, so that a medical table which assures high safety in moving the top plate manually can be realized.

According to the eleventh aspect, the X-ray imaging apparatus having a medical table in which a top plate for a patient to lie on is supported by a pedestal base in a manner to be able to move parallel to a plate surface, and a photographing device for X-raying a patient lying on the medical table, includes a detecting device for detecting that fingers holding the top plate are about to collide against the pedestal base when moving the top plate, and a stopping device for stopping movement of the top plate according to a detection signal from the detecting device, so that the X-ray imaging apparatus having a medical table which assures high stability in moving the top plate manually can be realized.

According to the second or twelfth aspect, the detecting device has a travel sensor that senses the fingers' travel toward a direction of collision against the pedestal base, so that a situation that the fingers are about to collide can be detected properly.

According to the third or thirteenth aspect, the travel sensor includes a linearly moving member which is given a recovery force by a spring, and a shift sensor which senses shift of the linearly moving member, so that the fingers' travel toward the direction of collision against the pedestal base can be detected properly.

According to the fourth or fourteenth aspect, the linearly moving member has a contact plate for the fingers at one end, so that traveling fingers can be received properly.

According to the fifth or fifteenth aspect, the contact plate has a cushion member on a surface of it, so that it gives a good feel when fingers touch it.

According to the sixth or sixteenth aspect, the cushion member is made of rubber, so that a good cushioning effect is achieved.

According to the seventh or seventeenth aspect, the shift sensor senses shift of the other end of the linearly moving member, so that the linearly moving member can be easily supported through the use of a middle portion.

According to the eighth or eighteenth aspect, the shift sensor is an optical sensor, so that it can make a detection in a noncontact manner.

According to the ninth or nineteenth aspect, the optical sensor includes a light-emitting element and a light-receiving element that face each other with a clearance between them, and a light-shielding element which enters or leaves the clearance, so that noncontact detection can be made properly.

According to the tenth or twentieth aspect, the light-emitting element and the light-receiving element are fixed in position, and the light-shielding element moves together with the other end of the linearly moving member, so that the position of the linearly moving member can be detected properly.

Further objects and advantages of the present invention will be apparent from the following description of the preferred embodiments of the invention as illustrated in the accompanying drawings.

BRIEF DESCRIPTION OF THE DRAWINGS

FIGS. 7(a) and 7(b) are explanatory views concerning manual movement of the top plate.

DETAILED DESCRIPTION OF THE INVENTION

Figure 1:
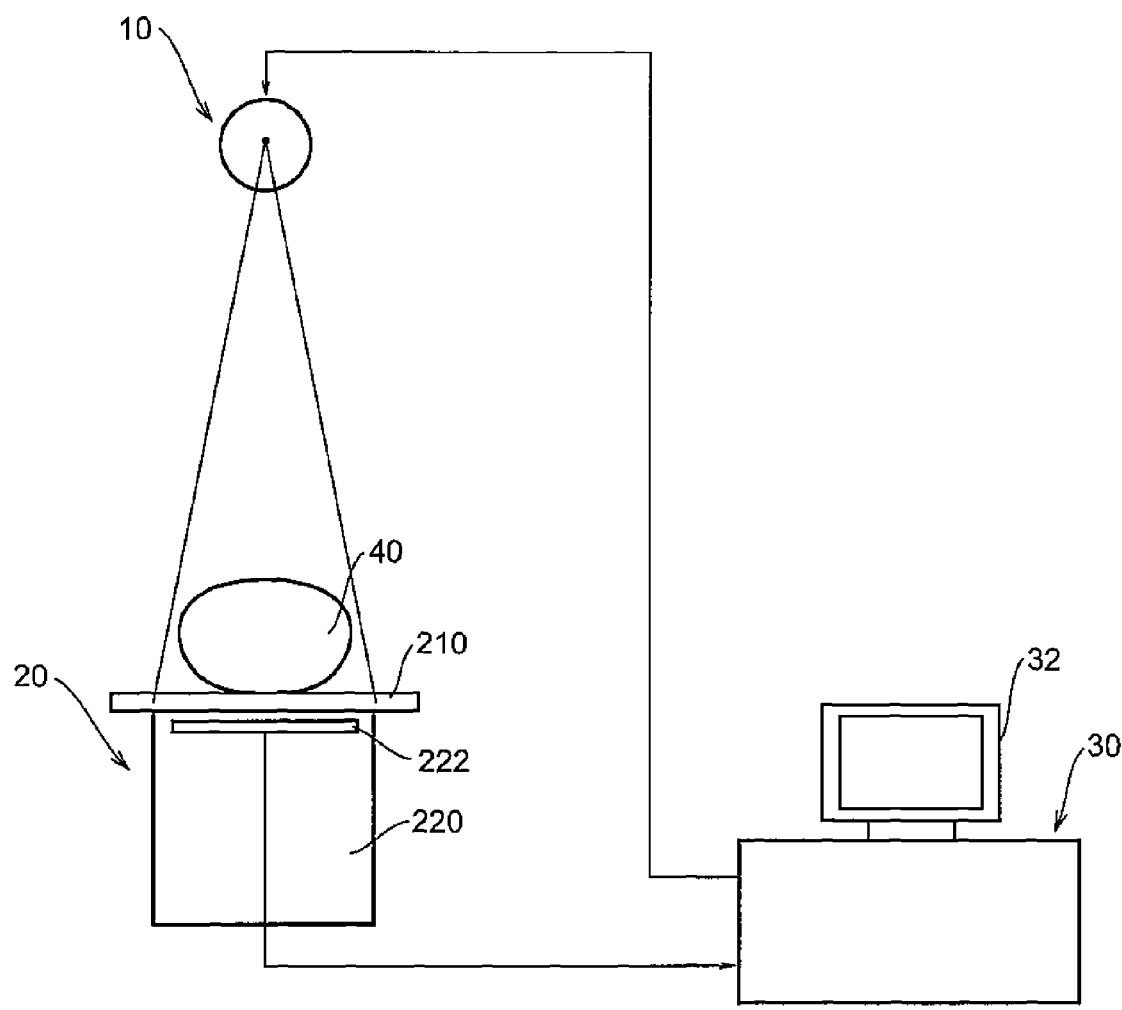
FIG. 1 is a view showing the structure of an X-ray imaging apparatus.

Next, various embodiments of the invention will be described in detail referring to drawings. The invention is not limited to the embodiments described herein. FIG. 1 shows a schematic structure of an X-ray imaging apparatus.

As shown in FIG. 1, the X-ray imaging apparatus includes an X-ray radiator 10, a photographing table 20 and an operator console 30. The photographing table 20 is so structured that a pedestal base 220 supports a top plate 210. A patient 40 is made to lie on the top plate 210. The pedestal base 220 incorporates an X-ray receiver 222. The X-ray radiator 10 and the X-ray receiver 222 face each other so that the patient 40 on the top plate 210 is X-rayed.

An optical signal received by the X-ray receiver 222 is inputted into the operator console 30. The operator console 30 reconstructs a fluoroscopic image according to the input signal and shows it on a display 32. An X-ray film cassette may be used instead of the X-ray receiver 222 to take a fluoroscopic image directly.

The operator console 30 also controls the X-ray radiator 10. It controls the intensity of X rays so that the brightness of fluoroscopic images shown on the display 32 is constant. Intensity control of X rays is done by controlling the tube voltage or tube current of the X-ray tube of the X-ray radiator 10.

The X-ray radiator 10, X-ray receiver 222 and operator console 30 are examples of the photographing device in the invention. The photographing table 20 is an example of the medical table in the invention. Also, the photographing table 20 is an example of the best mode of carrying out the invention. The structure of the photographing table 20 shows the best mode for carrying out the invention concerning a medical table.

Figure 2:
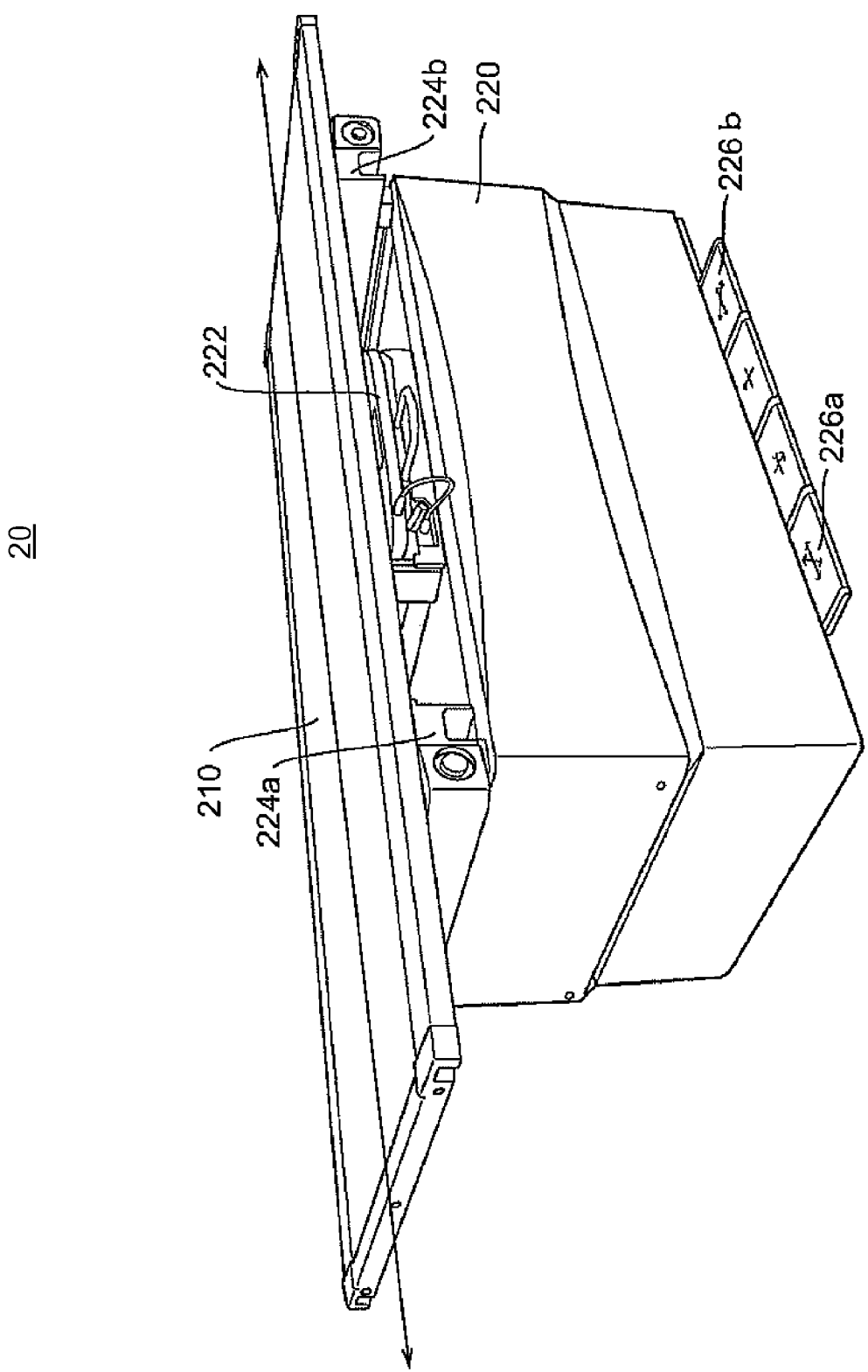
FIG. 2 is a view showing the external appearance of a medical table that may be used with the X-ray imaging apparatus shown in FIG. 1.

FIG. 2 shows the external appearance of the photographing table 20. The top plate 210 is a rectangular plane structure and the pedestal base 220 is an almost rectangular parallelepiped box structure. The X-ray receiver 222 is located in an upper part of the pedestal base 220 in a manner to face the back of the top plate 210. Hereinafter the direction parallel to the longer edge of the top plate is called the longitudinal direction and the direction parallel to its shorter edge is called the lateral direction.

The pedestal base 220 has a pair of support beams 224a, 224b. The support beams 224a, 224b are laterally extending beams which support the top plate 210 movably. The direction in which the top plate 210 can move is the longitudinal direction as indicated by the arrow.

Usually the top plate 210 is locked by a brake mechanism in the pedestal base 220 so that it is unmovable. Hereinafter the unmovable state is called the locked state. The locked state is cancelled by depressing either of left and right floating pedals 226a, 226b at the bottom of the pedestal base 220. The same floating pedals are provided on the opposite side.

Cancellation of the locked state is made only while the floating pedal 226a or 226b is being depressed and in the meantime the top plate 210 is movable. Hereinafter the movable state is called the floating state. The top plate 210 is moved manually while it is in the floating state.

Locking and floating of the top plate 210 are controlled by a control circuit in the pedestal base 220. The control circuit controls locking and floating of the top plate 210 according to an input signal from the floating pedal 226a, 226b and an input signal from a journey sensor that will be described later.

Figure 3:
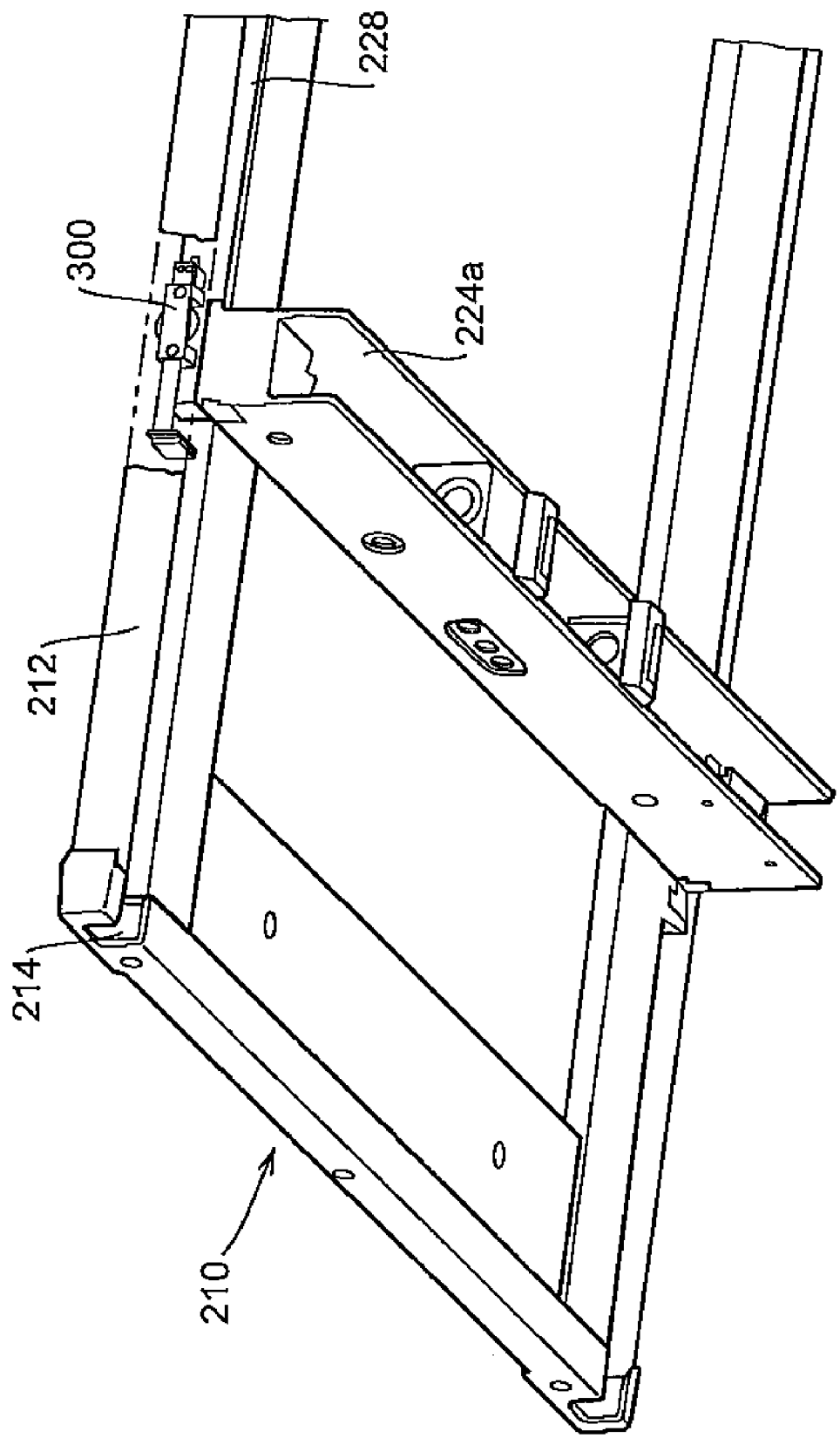
FIG. 3 is a view showing a partial structure of the medical table shown in FIG. 2.

FIG. 3 shows the relation between the top plate 210 and the support beam 224a. FIG. 3 is a view of the combination of the top plate 210 and the support beam 224a as obliquely seen from below. As shown in FIG. 3, a guide rail 228 is longitudinally attached to the upper side of one end of the support beam 224a. The end face of the guide rail 228 is on an extension plane of the left side of the support beam 224a.

A longitudinal frame 212 of the top plate 210 is engaged with the guide rail 228 through a groove 214. The other end of the support beam 224a is structured in the same way. The relation between the support beam 224b and the top plate 210 is the same as above.

Inside the groove 214, a journey sensor 300 is attached to the side face of the guide rail 228. The tip of the journey sensor 300 protrudes from the end face of the guide rail 228 toward the left end of the top plate 210. A journey sensor is also provided on the other end of the support beam 224a in the same way. Furthermore, the same journey sensors are provided on both ends of the support beam 224b respectively. Their tips protrude toward the right end of the top plate 210.

Figure 4:
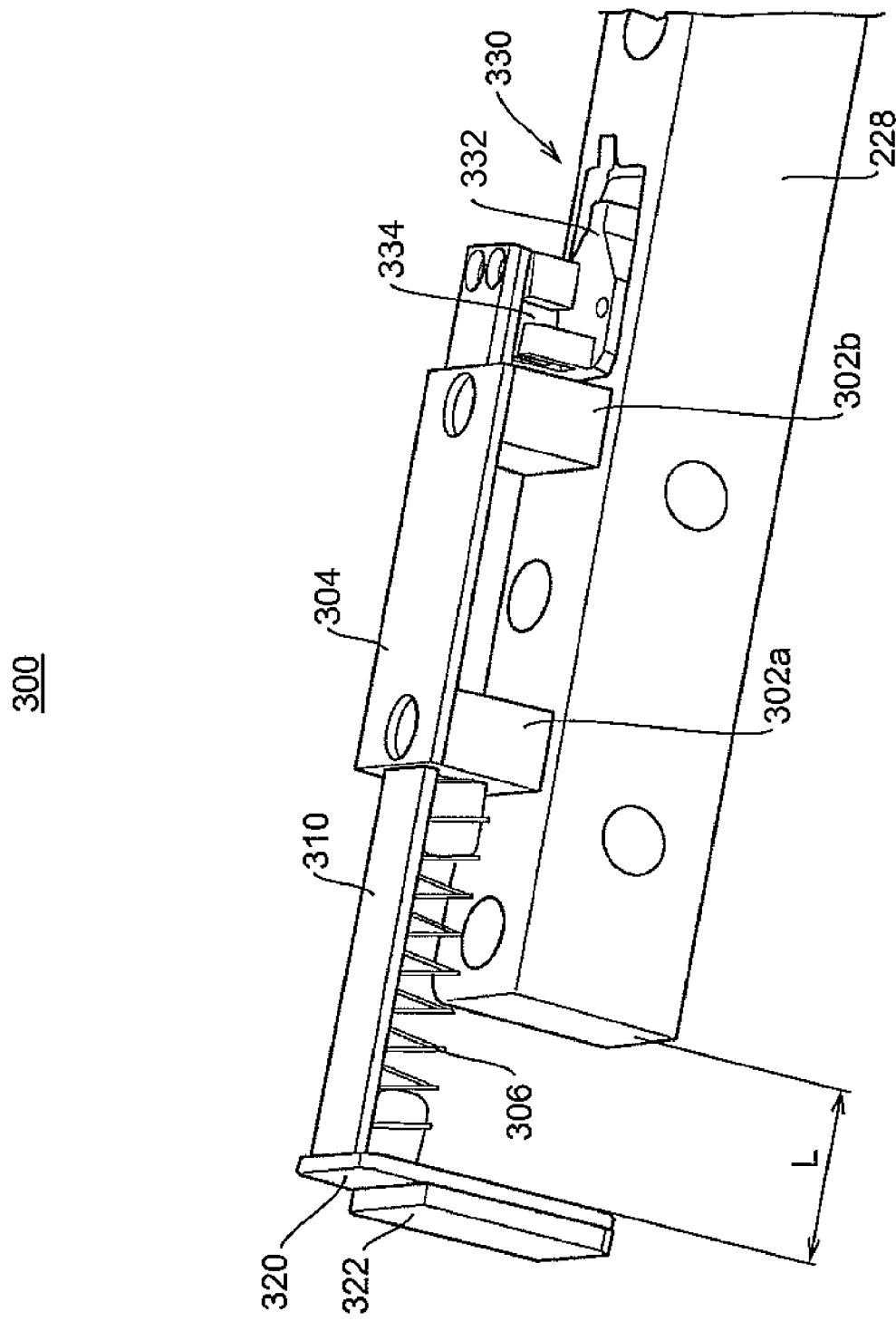
FIG. 4 is a view showing the structure of a journey sensor.

FIG. 4 shows the structure of the journey sensor 300. The journey sensor 300 is an example of the travel sensor in the invention. As shown in FIG. 4, the journey sensor 300 has a pair of support blocks 302a, 302b. The support blocks 302a, 302b are fixed on a side face of the guide rail 228 with an interval between them, The tips of the support blocks 302a, 302b are connected by a flat plate 304.

A slider 310 is supported by the support blocks 302a, 302b in a manner to be able to move parallel to the guide rail 228. The slider 310 is an example of the linearly moving member in the invention. The slider 310 is a long and thin rectangular plate member penetrating through holes in the tips of the support blocks 302a, 302b. Both ends of the slider 310 protrude outward from the support blocks 302a, 302b respectively.

The slider 310 has a stopper plate 320 at its left end. The stopper plate 320 is an example of the contact plate in the invention. The stopper plate 320 is orthogonally attached to the slider 310 in a manner that its back side faces the end face of the guide rail 228. A cushion member 322 is provided on the front side of the stopper plate 320. The cushion member 322 is an example of the cushion member in the invention. For example, a rubber plate is used as the cushion member 322. The material of the cushion member 322 is not limited to rubber but may be any other suitable soft material such as plastics.

A coil spring 306 is provided between the back side of the stopper plate 320 and the support block 302a. Therefore, the slider 310 is pushed to the left by the elastic force of the coil spring 306. This generates an interval L between the back side of the stopper plate 320 and the end face of the guide rail 228. This interval L is a range within which the slider 320 can shift.

A shift sensor 330 for detecting shift of the slider 310 is provided at the right end side of the slider 310. The shift sensor 330 is an example of the shift sensor in the invention. The shift sensor 330 is included, for example, of an optical sensor 332 and a light-shielding element 334.

Figure 5:
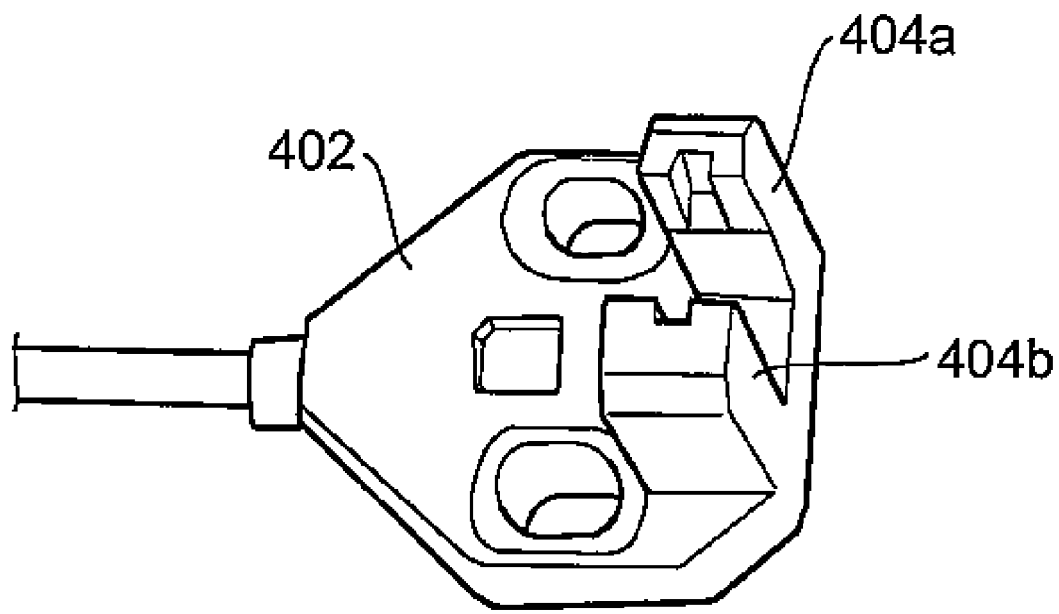
FIG. 5 is a view showing the structure of an optical sensor.

As shown in FIG. 5, the optical sensor 332 is a pair of columns 404a, 404b, vertically standing from a base 402, in which a light-emitting element and a light-receiving element, facing each other, are provided respectively. This optical sensor 332 is mounted on the side face of the guide rail 228 with its front side up and the light-shielding element 334 is mounted at the right end of the slider 310 in a manner to interrupt the light path for the optical sensor 332.

While the light-shielding element 334 is interrupting the light path, the optical sensor 332 does not sense light and thus the journey sensor 300 is inactive; however, as the slider 310 shifts to the right and the light-shielding element 334 gets out of the light path, the optical sensor 332 senses light and the journey sensor 300 becomes active.

Therefore, whether or not the slider 310 has shifted is known according as whether the journey sensor 300 is active or inactive. The journey sensor 300 becomes active upon shift of the slider 310 where the shift is shorter than distance L.

Figure 6:
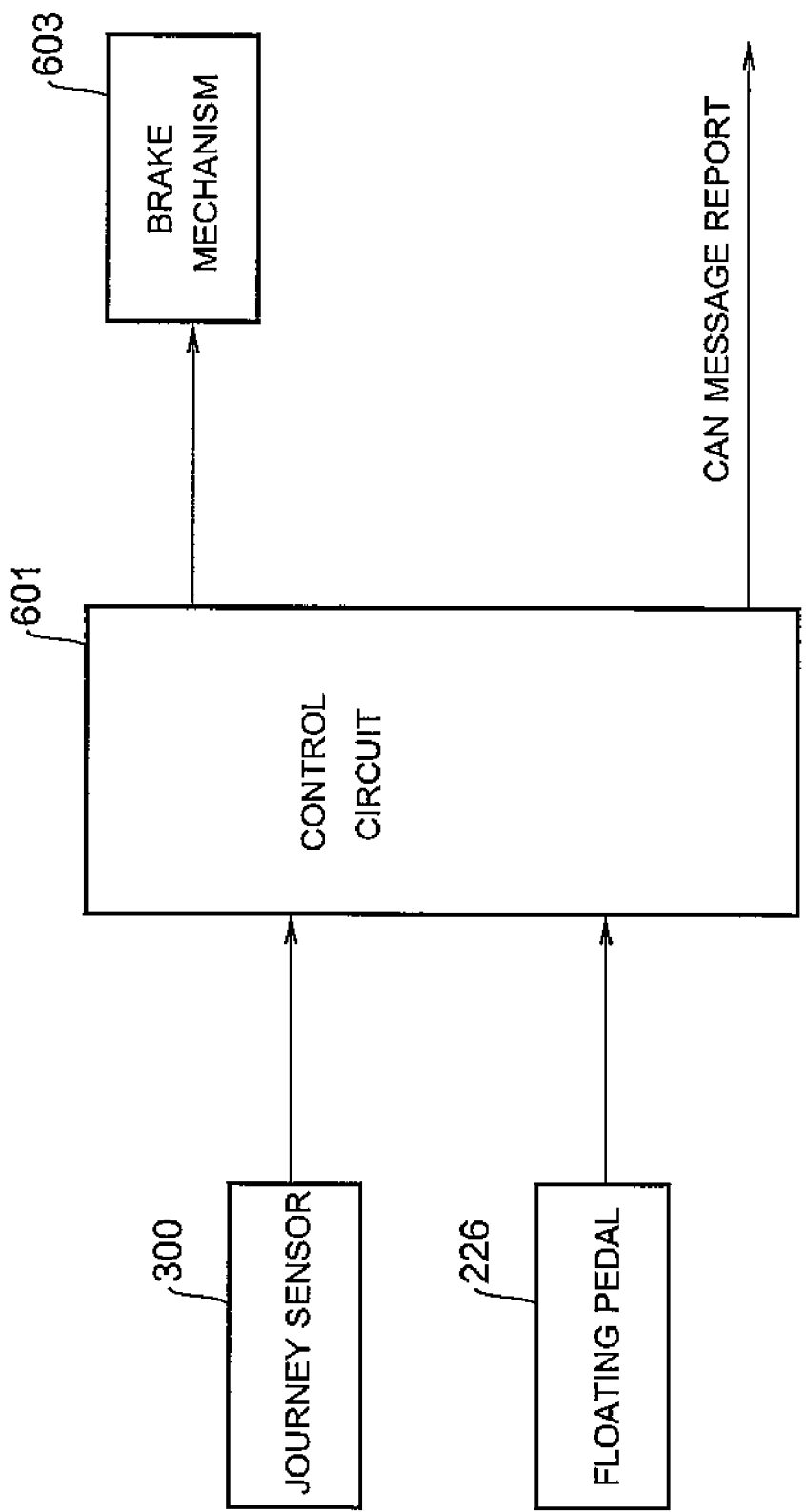
FIG. 6 is a block diagram of a top plate control system.

FIG. 6 is a block diagram of a top plate control system. As shown in FIG. 6, the top plate control system has a control circuit 601. The control circuit 601 is comprised of a digital logic circuit, a microcomputer and so on.

The control circuit 601 controls the brake mechanism 603 according to signals from the floating pedal 226 and the journey sensor 300. The control circuit 601 also sends a CAN message report (Controller Area Network message report) to the operator console 30. The journey sensor 300 is an example of the detecting device in the invention. The control circuit 601 and the brake mechanism 603 are examples of the stopping device in the invention.

The control circuit 601 controls the brake mechanism 603 in accordance with the following logic.

When the floating pedal is not depressed, the brake is activated and the top plate is locked.

When the floating pedal is depressed and the journey sensor is inactive, the brake is released and the top plate is floating.

When the floating pedal is depressed and the journey sensor is active, the brake is activated and the top plate is locked.

How this control system controls the top plate will be explained below. As shown in FIG. 7(a), when the top plate 210 is in a middle position, depression of the floating pedal 226a (or 226b) brings the top plate 210 into its floating state so that it is possible to move it in the longitudinal direction holding one of the four corners A, B, C, and D.

For example, if an operator holds the corner A and moves the top plate 210 to the right to a large extent, the operator's fingers will become on the verge of colliding against the guide rail 228's end face or the support beam 224a. However, since the journey sensor 300 is provided on the guide rail 228 and the stopper plate 320 at its tip protrudes forward from the end face of the guide rail 228, the stopper plate 320 first touches the fingers.

Since the surface of the stopper plate 320 is covered by the cushion member 322, it gives a good feel upon being touched; and also the coil spring 306 shrinks and the stopper plate 320 moves back together with the slider 310, thereby cushioning the shock. Consequently when it is touched, it does not damage the fingers.

When the light-shielding element 334 gets out of the light path for the optical sensor 332 as the slider 310 moves back, the journey sensor 300 becomes active and accordingly the control circuit 601 activates the brake. This hampers further movement of the top plate 210, thereby preventing the fingers from colliding against, or being caught by, the guide rail 228 or support beam 224a. The same is also true when the operator holds corner B, C, or D of the top plate 210 to move it.

Many widely different embodiments of the invention may be configured without departing from the spirit and the scope of the invention. It should be understood that the present invention is not limited to the specific embodiments described in the specification, except as defined in the appended claim.

What is claimed is:

1. A medical table comprising:
   a top plate for a patient to lie on, said top plate supported by a pedestal base and configured to move parallel to a plate surface;
   a detecting device configured to detect that fingers holding said top plate are about to collide against said pedestal base when moving said top plate, said detecting device comprising a travel sensor configured to sense travel of the fingers in a direction of collision against said pedestal base, said travel sensor comprising:
      a linearly moving member including a spring providing a recovery force; and
      a shift sensor configured to sense a shift of said linearly moving member; and
   a stopping device configured to stop movement of said top plate according to a detection signal generated by said detecting device.

2. The medical table according to claim 1, wherein said linearly moving member comprises a contact plate for the fingers at a first end.

3. The medical table according to claim 2, wherein said contact plate comprises a cushion member on a surface thereof.

4. The medical table according to claim 3, wherein said cushion member comprises rubber.

5. The medical table according to claim 2, wherein said shift sensor is configured to sense a shift of a second end of said linearly moving member opposite said first end.

6. The medical table according to claim 5, wherein said shift sensor comprises an optical sensor.

7. The medical table according to claim 6, wherein said optical sensor comprises:
   a light-emitting element and a light-receiving element that faces said light-emitting element with a clearance therebetween; and
   a light-shielding element configured to at least one of enter the clearance and leave the clearance.

8. The medical table according to claim 7, wherein:
   said light-emitting element and said light-receiving element are fixed in position; and
   said light-shielding element is configured to move together with said second end of said linearly moving member.

9. An X-ray imaging apparatus comprising:
   a medical table comprising a top plate for a patient to lie on, said top plate supported by a pedestal base and configured to move parallel to a plate surface;
   a photographing device configured to transmit X-rays toward the medical table;
   a detecting device configured to detect that fingers holding said top plate are about to collide against said pedestal base when moving said top plate, said detecting device comprising a travel sensor comprising:
      a linearly moving member including a spring providing a recovery force; and
      a shift sensor configured to sense a shift of said linearly moving member; and
   a stopping device configured to stop movement of said top plate according to a detection signal generated by said detecting device.

10. The X-ray imaging apparatus according to claim 9, wherein said travel sensor is configured to sense the fingers' travel toward a direction of collision against said pedestal base.

11. The X-ray imaging apparatus according to claim 9, wherein said linearly moving member comprises a contact plate for the fingers at a first end.

12. The X-ray imaging apparatus according to claim 11, wherein said contact plate comprises a cushion member on a surface thereof.

13. The X-ray imaging apparatus according to claim 12, wherein said cushion member comprises rubber.

14. The X-ray imaging apparatus according to claim 11, wherein said shift sensor is configured to sense a shift of a second end of said linearly moving member opposite said first end.

15. The X-ray imaging apparatus according to claim 14, wherein said shift sensor comprises an optical sensor.

16. The X-ray imaging apparatus according to claim 15, wherein said optical sensor comprises:
   a light-emitting element and a light-receiving element that faces said light-emitting element with a clearance therebetween; and
   a light-shielding element configured to at least one of enter the clearance and leave the clearance.

17. The X-ray imaging apparatus according to claim 16, wherein:
   said light-emitting element and said light-receiving element are fixed in position; and
   said light-shielding element is configured to move together with said second end of said linearly moving member.

* * * * *